United States Patent [19]

Davenport

[11] Patent Number: 4,675,449
[45] Date of Patent: Jun. 23, 1987

[54] PROCESS FOR PRODUCING 6-HYDROXY-2-NAPHTHONES

[75] Inventor: Kenneth G. Davenport, Corpus Christi, Tex.

[73] Assignee: Celanese Corporation, New York, N.Y.

[21] Appl. No.: 870,062

[22] Filed: Jun. 3, 1986

[51] Int. Cl.$^4$ ............................................. C07C 45/54
[52] U.S. Cl. ................................................. 568/319
[58] Field of Search ............................. 568/319, 333

[56] References Cited

U.S. PATENT DOCUMENTS

| 2,763,691 | 9/1958 | Knowles | 568/319 |
| 2,833,825 | 5/1958 | Lewis | 568/335 |
| 3,403,183 | 9/1968 | Dobraty et al. | 568/319 |
| 4,593,125 | 6/1986 | Davenport et al. | 568/319 |
| 4,599,452 | 7/1986 | Calquhoun et al. | 568/319 |
| 4,604,485 | 8/1986 | Calquhoun | 568/319 |
| 4,607,125 | 8/1986 | Mott | 568/319 |

FOREIGN PATENT DOCUMENTS 2616986  10/1977  Fed. Rep. of Germany ...... 568/319

OTHER PUBLICATIONS

Simons et al., J.A.C.S., vol. 62, pp. 485–486 (1940).
Joshi et al, J. Indian Chem. Soc., vol. 29, pp. 225–232 (1952).

Primary Examiner—James H. Reamer
Attorney, Agent, or Firm—M. Turken; D. R. Cassady

[57] ABSTRACT

A process is provided for the production of 6-hydroxy-2-naphthones, e.g., 6-hydroxy-2-acetonaphthone, by contacting a 2-naphthyl carboxylate ester, e.g., 2-naphthyl acetate with at least 20 moles of hydrogen fluoride per mole of 2-naphthyl ester, at reaction temperatures, e.g., 0° to 100° C. for a period of reaction, e.g., 30 minutes to 8 hours sufficient to produce the desired amount of 6-hydroxy-2-naphthone. The process may utilize a carboxylic acid or anhydride, e.g., acetic acid or anhydride as an additive for the purpose of further increasing the regioselectivity of the 6-hydroxy-2-naphthone product. The process is capable of being carried out at a conversion of 2-naphthyl ester of at least 90% and a regioselectivity to 6-hydroxy-2-naphthone of at least 90 mol %.

9 Claims, No Drawings

PROCESS FOR PRODUCING 6-HYDROXY-2-NAPHTHONES

This invention relates to a process for producing 6-hydroxy-2-naphthones such as 6-hydroxy-2-acetonaphthone.

BACKGROUND OF THE INVENTION

6-Hydroxy-2-naphthones such as 6-hydroxy-2-acetonaphthone (6,2-HAN) are possible intermediates for a variety of products having a multiplicity of end uses. Thus, U.S. Pat. No. 4,524,217 issued June 18, 1985, discloses the use of hydroxy aromatic ketones, where the aromatic group may be 2,6-naphthylene, as intermediates for the production of N-acyl-acyloxy aromatic amines which can be used for the preparation of poly(ester-amide)s capable of forming an anisotropic melt phase and suitable for being formed into shaped articles such as moldings, fibers and films. Pending U.S. application Ser. No. 06/633,832, filed July 24, 1984, discloses a process wherein hydroxy aromatic ketones, e.g., 6,2-HAN, are used to produce acyloxy aromatic carboxylic acids such as 6-acetoxy-2-naphthoic acid (6,2-ANA) which are also capable of being used directly to make polymers which can be formed into an anisotropic melt suitable for the formation of shaped articles. Pending U.S. applications Ser. No. 06/661,552, filed Oct. 17, 1984, and Ser. No. 06/689,533, filed Jan. 7, 1985, disclose processes wherein hydroxy aromatic ketones such as 6,2-HAN are used as intermediates for the production of aromatic diols such as 2,6-dihydroxynaphthalene and their esters and ethers which have utility as polymerization monomers, photographic developers, polymerization inhibitors, dye intermediates, and anti-oxidants.

Davenport, U.S. Pat. No. 4,593,125, teaches the acylation of 2-substituted naphthalenes, e.g., 2-naphthol, with anhydrous hydrogen fluoride as catalyst, to obtain 6-substituted-2-naphthones such as 6-hydroxy-2-acetonaphthone.

Lewis, U.S. Pat. No. 2,833,825 shows the rearrangement of esters of phenolic compounds, e.g., beta-naphthol, to hydroxyaryl alkyl ketones using anhydrous hydrogen fluoride as catalyst. The working examples of this patent are limited to the rearrangement of esters of higher fatty acids with the yields ranging from 55 to 95%.

Simons et al, Journal of the American Chemical Society, 62, 485 and 486 (1940) show the use of hydrogen fluoride as a condensing agent for various rearrangements and at page 486 show the Fries rearrangement of phenyl acetate to obtain p-hydroxyacetophenone.

Dann and Mylius in a dissertation included as part of a series of Reports from the Institute for Applied Chemistry of the University of Erlangen, received for publication on Jan. 7, 1954 and published in Annalen der Chemie 587 Band, pages 1 to 15, show the rearrangement of phenyl acetate in hydrogen fluoride to 4-hydroxyacetophenone, with a maximum yield of 81% after 24 hours of reaction time. They also report a yield of 92% from this reaction stated to be obtained by K. Weichert as reported in Angewandte Chemie 56, 338 (1943), but suggest that the difference in yields may be at least partly due to the previous ignoring by Weichert of the accompanying 2-hydroxyacetophenone. Dann and Mylius also report somewhat lower yields of hydroxy aromatic ketones from rearrangements in hydrogen fluoride of m-cresyl acetate, p-cresyl acetate, and guaiacol acetate.

Muessdoerffer and Niederprum in German Offenlegungschrift No. 2,616, 986, published Oct. 27, 1977, disclose the acylation of phenols and substituted phenols with an acyl chloride in the presence of hydrogen fluoride to yield the 4-acyl derivative in high yield with high selectivity. The inventors disclose that 2-naphthol and 7-chloro-2-naphthol can be acylated according to their invention but do not teach any specific method for the acylation of the naphthol derivatives nor do they indicate what isomer or isomers are produced with such naphthol derivatives.

SUMMARY OF THE INVENTION

In accordance with this invention, 6-hydroxy-2-naphthones are produced by the Fries rearrangement of 2-naphthyl carboxylate esters using hydrogen fluoride as catalyst, under reaction conditions so as to obtain unexpectedly high conversion of the 2-naphthyl ester and high selectivity to the 6,2-isomer concurrently. In particular, the process of this invention results in high regioselectivity to the 6,2 isomer, which is the molar percentage of conversion of 2-naphthyl carboxylate ester to the 6,2 isomer based on the conversion to all hydroxynaphthone isomers.

The preparation of 6-hydroxy-2-naphthones by the Fries rearrangement of 2-naphthyl carboxylate esters using hydrogen fluoride as catalyst proceeds in accordance with the following equation:

$$\text{ArOCOR} \xrightarrow{\text{HF}} \text{HO—Ar'—COR}$$

where Ar and Ar' are 2-naphthyl and 2,6-naphthylene respectively, either unsubstituted or with at least one ring hydrogen atom in the 1,3,4,5,7 or 8 positions substituted with a substituent which does not interfere with the reaction. Such substituents may be, for example, alkyl, alkenyl, alkynyl, alkoxy, or alkylthio containing 1 to 18, preferably 1 to 4 carbon atoms, aralkyl containing 7 to 18, preferably 7 to 10 carbon atoms; halogen, e.g., chlorine, bromine, or iodine; and R is a monovalent organic radical containing, for example, 1 to 18 carbon atoms preferably 1 to 4 carbon atoms. R may be, for example, alkyl, alkenyl, alkynyl, alkoxyalkyl, acylalkyl or acyloxyalkyl containing 1 to 18 carbon atoms, preferably 1 to 4 carbon atoms either unsubstituted or substituted with radicals such as halogen, e.g., chlorine, bromine, or iodine; or an aryl radical, e.g., phenyl or 1-, or 2-naphthyl, either unsubstituted or with one or more of its ring hydrogen atoms substituted with a substituent which does not interfere with the reaction, e.g., any of substituents previously mentioned in connection with Ar and Ar' and containing 1 to 12 carbon atoms. Most preferably Ar is unsubstituted 2-naphthyl, Ar' is unsubstituted 2,6-naphthylene, and R is methyl, such that the process involves the Fries rearrangement of 2-naphthyl acetate to 6-hydroxy-2-acetonaphthone (6,2-HAN) which proceeds in accordance with the following equation:

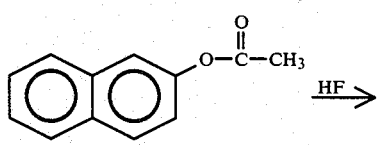

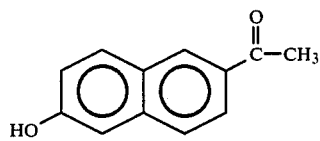

In carrying out the process so as to obtain particularly high yields of a 6-hydroxy-2-naphthone within this invention, a 2-naphthyl or substituted 2-naphthyl carboxylate ester is contacted with at least about 20 moles, preferably about 20 to 60 moles of hydrogen fluoride catalyst per mole of 2-naphthyl carboxylate ester generally at a temperature of about 0° to 100° C., preferably about 50° to 75° C., for a reaction period which is suitably about 30 minutes to 8 hours, preferably about 2 to 4 hours.

In some instances, the regioselectivity to the 6,2 isomer may be further improved by using as an additive, an alkanoic acid, e.g., containing 1 to 4 carbon atoms or an anhydride of such acid. If an additive is utilized it is preferably the same acid as the esterifying acid of the 2-naphthyl carboxylate ester or its anhydride, e.g., acetic acid or anhydride when 2-naphthyl acetate is the starting material. The additive may be used, for example in an amount of 0.1 to 2.0 moles, preferably 0.7 to 1.3 moles per mole of 2-naphthyl carboxylate ester.

The reaction is initiated by contacting the 2-naphthyl carboxylate ester, an additive for the reaction if used, such as acetic acid or anhydride, and hydrogen fluoride catalyst in a corrosion resistant reactor at the desired temperature of reaction for the desired period of reaction. For example, the 2-naphthyl ester and additive, if used may initially be charged to the reactor, hydrogen fluoride may then be charged at a temperature less than the specified reaction temperature and the reaction adjusted to the specified reaction temperature for the specified reaction period. The hydrogen fluoride may be charged as a liquid or a gas using technologies of handling well known to those skilled in the art. In carrying out the reaction, an inert gas such as nitrogen may be used to keep the reaction space under the desired pressure, about 2.5 to about 500 psig., thereby keeping sufficient HF in contact with the reacting liquid.

In general, the process of this invention results in a conversion of 2-naphthyl ester, e.g., 2-naphthyl acetate of at least about 90%, preferably at least about 95%, with a selectivity to 6-hydroxy-2-naphthone, e.g., 6,2-HAN of at least about 40%, preferably at least about 60%, and a regioselectivity to 6-hydroxy-2-naphthone of at least about 90%, preferably at least about 95%.

The process is capable of producing relatively high yields of 6-hydroxy-2-naphthone, e.g. 6,2-HAN, using relatively low ratios of hydrogen fluoride to naphthyl ester and low temperatures of reaction. This in turn results in a more economical purification of product and recycle of hydrogen fluoride, and an energy saving due to the low reaction temperatures which are employed.

DESCRIPTION OF SPECIFIC EMBODIMENTS

Examples 1 to 9

These examples further illustrate the process of the invention. In each of the examples, a 300 cc Hastelloy C autoclave was charged with a quantity of 2-naphthyl acetate. In Examples 7, 8 and 9, one mole of acetic anhydride per mole of 2-naphthyl acetate was also charged with the 2-naphthyl acetate. The autoclave was cooled to −50° C. and evacuated to 150 mm Hg whereupon a quantity of anhydrous hydrogen fluoride was transferred from a cylinder to the autoclave at such a rate that the temperature did not exceed 0° C. The contents were warmed to reaction temperature and stirred for a predetermined period of reaction during which time a pressure of ca. 40 psig was generated. At the end of the run, the hydrogen fluoride was vented through a caustic scrubber and the contents of the autoclave were poured onto ca. 30 g of ice. The pH of the mixture was adjusted to 6.5 using a solution of 50% potassium hydroxide and the mixture was then extracted with 75 mL of ethyl acetate (3×). The organic solution was dried over anhydrous MgSO$_4$, filtered, and the solvent was removed using a rotary evaporator to yield the 6-hydroxy-2-naphthone.

The conditions of reaction and analysis of the product for each example are shown in Table I which indicates temperature (T) and period (t) of reaction, moles of HF per mole of 2-naphthyl acetate (HF), conversion of 2-naphthyl acetate to all products (conv.), percent selectivities of 2-naphthyl acetate conversion to 2-naphthol (2-ol), 6-hydroxy-2-acetonaphthone (6,2-HAN), 6-acetoxy-2-acetonaphthone (6,2-AAN), 3-hydroxy-2-acetonaphthone (3,2-HAN), 2-hydroxy-1-acetonaphthone (2,1-HAN), and other hydroxyacetonaphthones (HAN), the yield of 6,2-HAN, including 6,2-AAN (6,2-HAN yield) which is either a GC or HPLC yield obtained by multiplying conversion of 2-naphthyl acetate (mole) times selectivity to 6,2-HAN plus 6,2-AAN (mole), regioselectivity of 6,2-HAN (6,2-HAN regiosel.) which is calculated by dividing the number of moles of 6,2-HAN produced by the sum of the moles of all isomers of hydroxyacetonaphthones produced and multiplying by 100, and carbon accountability (carbon acct.) which is the sum of the products detected by gas chromatography (GC) or high pressure liquid chromotography (HPLC). The notations "NA" indicates "not available" and "ND", "not determined".

TABLE I

| Example | T (°C.) | t (h) | HF | conv. | 2-ol | 6,2-HAN | 6,2-AAN | 3,2-HAN | 2,1-HAN | HAN | 6,2-HAN yield | 6,2-HAN regiosel. | carbon acct. |
|---|---|---|---|---|---|---|---|---|---|---|---|---|---|
| 1 | 60 | 2.0 | 26.6 | 98.8 | 23.8 | 47.3 | NA | 0.4 | 0.6 | ND | 46.7 | 97.9 | 72.6 |
| 2 | 60 | 2.0 | 33.3 | 99.7 | 6.9 | 44.9 | NA | 1.2 | 0.2 | ND | 44.8 | 97.8 | 69.8 |
| 3 | 60 | 5.8 | 33.3 | 99.7 | 9.6 | 43.2 | NA | 0.5 | 0.1 | 0.8 | 43.1 | 96.9 | 60.0 |
| 4 | 75 | 4.0 | 33.3 | 99.7 | 8.4 | 67.6 | NA | ND | ND | ND | 66.4 | 100.0 | 105.3 |
| 5 | 75 | 5.0 | 35.0 | 99.8 | 5.1 | 49.4 | NA | 0.7 | ND | 0.7 | 49.3 | 97.2 | 64.4 |
| 6 | 75 | 3.0 | 60.0 | 99.5 | 3.9 | 50.1 | 0.6 | 0.5 | 0.3 | 0.6 | 50.4 | 97.3 | 80.0 |
| 7 | 60 | 4.0 | 21.3 | 95.2 | 4.1 | 54.8 | 20.1 | 0.5 | 1.6 | ND | 71.3 | 98.6 | 98.0 |
| 8 | 60 | 4.0 | 22.0 | 97.3 | 4.0 | 59.7 | 12.5 | 0.7 | 0.3 | 0.8 | 70.3 | 97.6 | 86.4 |
| 9 | 75 | 4.0 | 33.3 | 99.9 | 0.4 | 44.4 | NA | 0.4 | ND | ND | 44.4 | 99.1 | 56.8 |

Examples 10 to 13

The procedure of Examples 1 to 9 was followed for these examples except that the time of reaction was constant at 2 hours. The conditions of reaction and analysis of the product are shown in Table II wherein unlike Table I, the yields of 6,2-HAN and 6,2-AAN are reported separately.

TABLE II

| Example | HF | T (°C.) | conv. | 2-ol | 2,1-HAN | 3,1-HAN | 6,2HAN | 6,2-HAN yield | 6,2-AAN | 6,2-AAN yield | 6,2-HAN regiosel |
|---|---|---|---|---|---|---|---|---|---|---|---|
| 10 | 20 | 50 | 84.0 | 22.0 | 8.3 | 0.4 | 44.0 | 37.0 | 4.5 | 3.8 | 83.5 |
| 11 | 30 | 50 | 85.5 | 24.6 | 4.0 | 0.5 | 42.7 | 36.5 | 4.2 | 3.6 | 90.5 |
| 12 | 30 | 75 | 98.7 | 8.0 | 0 | 0.6 | 44.6 | 44.0 | 0.2 | 0.2 | 98.7 |
| 13 | 40 | 75 | 99.7 | 5.2 | 0 | 0.5 | 43.7 | 43.5 | 0.3 | 0.3 | 98.8 |

Examples 14 to 18

The procedure of the previous examples was followed except that the reactor was charged with 2-naphthyl propionate rather than acetate. The conditions of reaction and analysis of the product are shown in Table III including, in addition to certain values indicated in the previous tables, percent selectivity of 2-naphthyl propionate conversion to 6-hydroxy-2-propionaphthone (6,2-HPN) and the yield of the latter compound (6,2-HPN yield).

TABLE III

| Example | HF | T (°C.) | time (min.) | conv. | 2-ol | 6,2-HPN | 6,2-HPN yield |
|---|---|---|---|---|---|---|---|
| 14 | 50 | 75 | 120 | 100 | 6.7 | 43.8 | 43.8 |
| 15 | 50 | 50 | 120 | 91.9 | 29.2 | 37.2 | 34.2 |
| 16 | 50 | 75 | 60 | 98.9 | 17.7 | 44.7 | 44.2 |
| 17 | 75 | 75 | 60 | 97.9 | 18.8 | 28.3 | 27.7 |
| 18 | 75 | 75 | 120 | 98.5 | 15.4 | 44.9 | 44.2 |

Examples 19 to 23

The procedure of the previous examples was followed except that the reactor was charged with 2-naphthyl n-butyrate and the temperature of reaction was constant at 75° C. The conditions of reaction and analysis of the product are shown in Table IV including, in addition to certain values presented in the previous tables, percent selectivities to 6-hydroxy-2-n-butyronaphthone (6,2-HBN) and 6-n-butoxy-2-n-butyronaphthone (6,2-BBN) and yields of the latter compounds ("6,2-HBN yield" and "6,2-BBN yield," respectively).

TABLE IV

| Example | HF | time (min.) | conv. | 2-ol | 6,2-HBN | 6,2-BBN | 6,2-HBN yield | 6,2-BBN yield |
|---|---|---|---|---|---|---|---|---|
| 19 | 50 | 60 | 95.7 | 22.2 | 26.2 | 1.1 | 25.1 | 1.0 |
| 20 | 50 | 120 | 98.7 | 13.7 | 48.1 | 0.6 | 47.5 | 0.5 |
| 21 | 75 | 60 | 97.0 | 25.0 | 29.7 | 0.9 | 28.9 | 0.9 |
| 22 | 75 | 120 | 99.0 | 15.7 | 32.6 | 0.6 | 32.2 | 0.6 |
| 23 | 75 | 180 | 98.9 | 14.3 | 37.1 | 0.3 | 36.7 | 0.3 |

In examples 14 to 23, examination of the product by gas/liquid chromotography and mass spectography indicated that the 6-hydroxy-2-naphthone was produced in substantially greater amount than the total of all the other hydroxynaphthone isomers.

The results of the examples indicate that the process of the invention may be used to produce 6-hydroxy-2-naphthones from 2-naphthyl carboxylate esters at high rates of 2-naphthyl ester conversion and 6-hydroxy-2-naphthone regioselectivity.

I claim:

1. A process comprising contacting a 2-naphthyl carboxylate ester with at least about 20 moles of hydrogen fluoride per mole of 2-naphthyl ester at reaction temperature to produce a 6-hydroxy-2-naphthone.

2. The process of claim 1 wherein the reaction proceeds in accordance with the following equation:

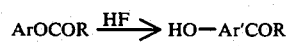

wherein Ar is 2-naphthyl, Ar' is 2,6-naphthylene and R is alkyl containing 1 to 4 carbon atoms.

3. The process of claim 2 wherein about 20 to 60 moles of hydrogen fluoride per mole of 2-naphthyl ester are utilized and the reaction is carried out at a temperature of about 0° to 100° C., for a period of about 30 minutes to 8 hours.

4. The process of claim 3 wherein said 2-naphthyl carboxylate ester is 2-naphthyl acetate and said 6-hydroxy-2-naphthone is 6-hydroxy-2-acetonaphthone.

5. The process of claim 4 carried out at a temperature of about 50° to 75° C. for a reaction period of about 2 to 4 hours.

6. The process of claim 4 carried out in the presence of 0.1 to 2 moles of acetic acid or acetic anhydride per mole of 2-naphthyl acetate, as a reaction additive.

7. The process of claim 4 wherein the percent conversion of 2-naphthyl acetate is at least 90% and the regioselectivity to 6-hydroxy-2-acetonaphthone is at least 90 mol % based on the total of all the hydroxyacetonaphthones produced.

8. The process of claim 3 wherein the pressure employed is from about 2.5 to about 500 psig.

9. The process of claim 5 wherein the pressure employed is from about 2.5 to about 500 psig.

* * * * *